United States Patent [19]
Guigan

[11] Patent Number: 5,110,552
[45] Date of Patent: May 5, 1992

[54] APPARATUS FOR PERFORMING BIOLOGICAL ANALYSES BY CHEMICAL REACTION ON A SERUM

[76] Inventor: Jean Guigan, 5, rue des Ursulines, 75005 Paris, France

[21] Appl. No.: 381,430

[22] Filed: Jul. 18, 1989

[30] Foreign Application Priority Data

Jul. 28, 1988 [FR] France .............................. 88 10212

[51] Int. Cl.⁵ ...................... G01N 21/00; G01N 35/00
[52] U.S. Cl. ........................................ 422/64; 422/72; 422/100; 422/102; 436/45; 356/246; 356/427; 494/16; 494/21
[58] Field of Search ................. 422/64, 72, 100, 102; 436/45; 356/246, 427; 494/16, 21

[56] References Cited

U.S. PATENT DOCUMENTS

| | | |
|---|---|---|
| 3,497,320 | 2/1970 | Blackburn . |
| 4,119,407 | 10/1978 | Goldstein et al. ................. 422/101 |
| 4,135,883 | 1/1979 | McNeit et al. ......................... 422/55 |
| 4,387,164 | 6/1983 | Hevey et al. ........................... 436/45 |
| 4,387,992 | 6/1983 | Swartz ................................. 356/246 |
| 4,390,499 | 6/1983 | Curtis et al. ........................... 422/64 |
| 4,456,581 | 6/1984 | Edelmann et al. ................... 356/246 |
| 4,657,869 | 4/1987 | Richards et al. ..................... 436/810 |
| 4,676,952 | 6/1987 | Edelmann et al. ..................... 436/45 |
| 4,690,801 | 9/1987 | Anderson ............................. 422/102 |
| 4,726,683 | 2/1988 | Nebuloni ............................. 356/257 |

FOREIGN PATENT DOCUMENTS 2351022 12/1977 France .

*Primary Examiner*—Robert J. Warden
*Assistant Examiner*—Stephanie Blythe
*Attorney, Agent, or Firm*—Sughrue, Mion, Zinn Macpeak & Seas

[57] ABSTRACT

The apparatus of the invention includes a plurality of cartridges (1) each containing serum, and reagents in a sachet. The cartridges are inserted into the automatic processing device (40) enabling the serum to be put into contact with the various reagents and then enabling the results to be read.

8 Claims, 10 Drawing Sheets

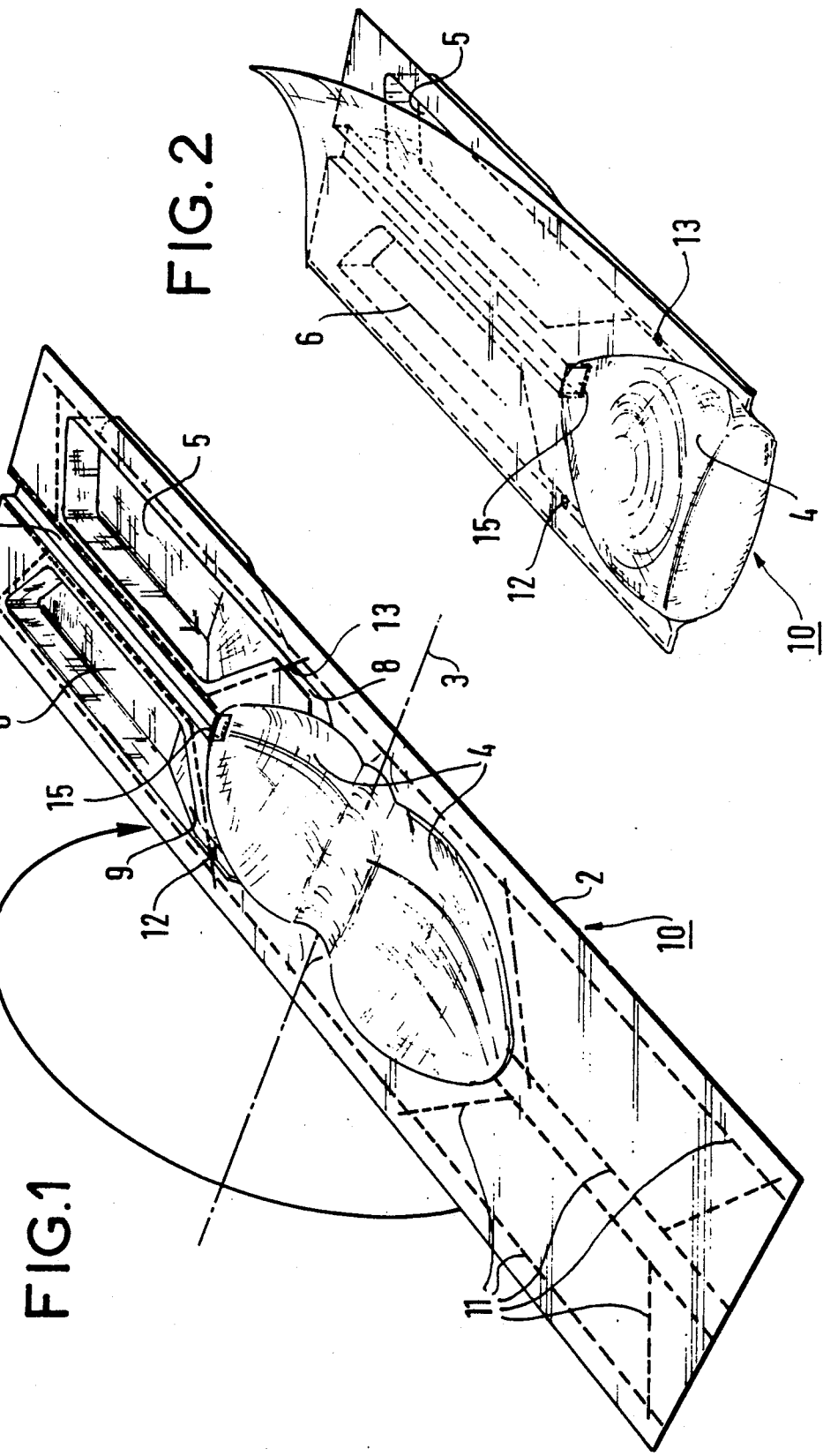

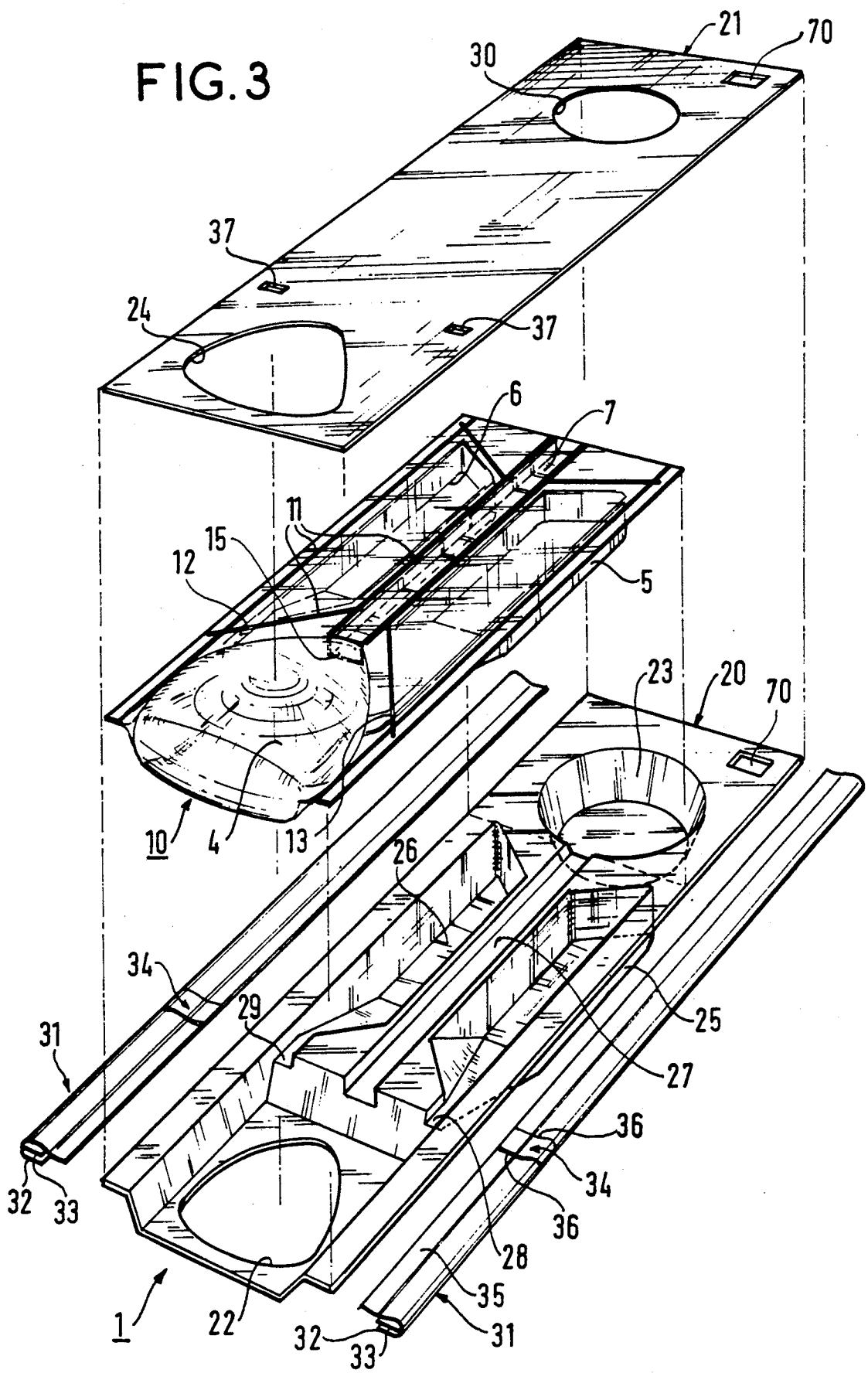

FIG.6 FIG.7
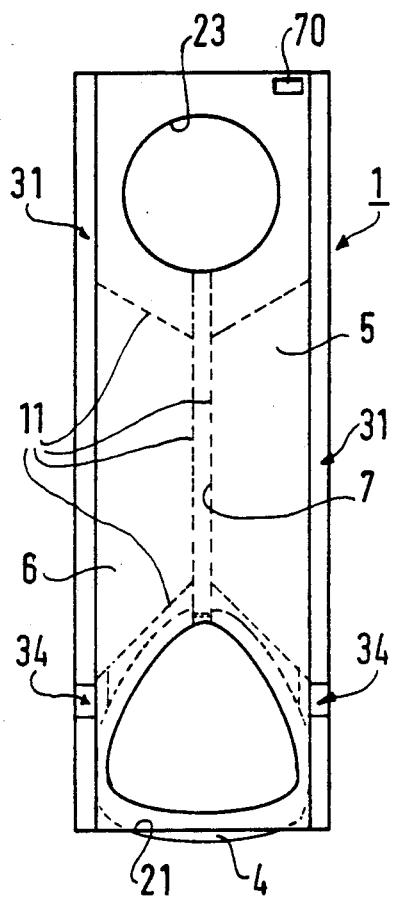
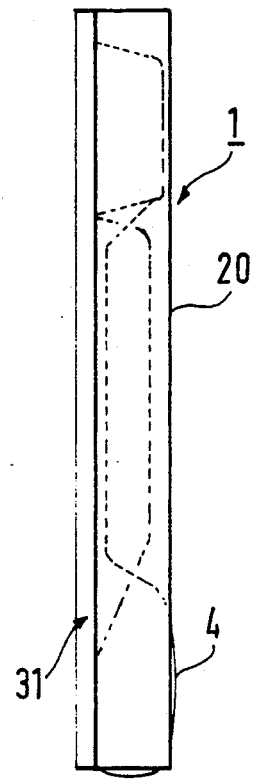
FIG.8
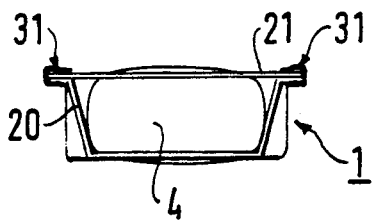
FIG.9
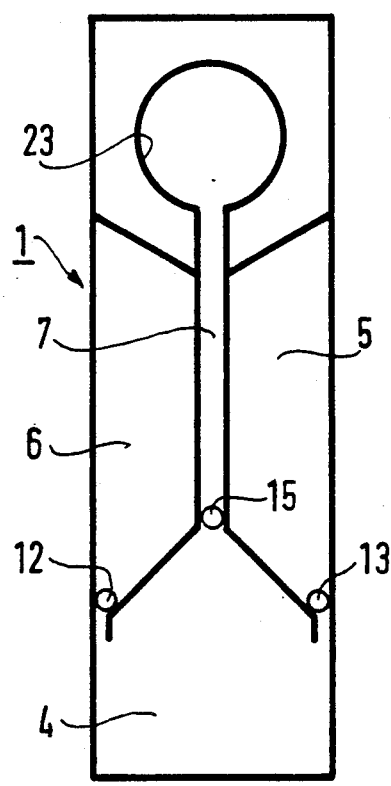

APPARATUS FOR PERFORMING BIOLOGICAL ANALYSES BY CHEMICAL REACTION ON A SERUM

The present invention relates to apparatus for performing biological analyses by chemical reaction on a serum.

BACKGROUND OF THE INVENTION

In general, the technique is to insert a certain quantity of a sample of serum into a reaction cuvette by means of a manual or an automatic pipette. Thereafter, a pipette is used to add one, two, or three reagents or diluants, depending on the analysis and taken from flasks containing said substances. This means that each time they are used, the pipettes must be washed out and numerous manipulations of reagent flasks are required.

The object of the present invention is to avoid this drawback and to provide a compact device enabling an operator to perform a large number of different analyses easily and quickly.

SUMMARY OF THE INVENTION

The present invention provides apparatus for performing biological analyses by chemical reaction on a serum, the apparatus comprising a processing device for simultaneously processing a plurality of cartridges, and comprising:

a hub associated with a motor having an angle encoder for controlling rotation cycles and suitable for imparting both rapid centrifuging motion to the hub and also slow step-by-step motion thereto;

a plurality of cartridge-carrying lifts fixed radially to the hub and means for causing each of them to pass from a high, "cartridge-loading" position to a low, "working" position, each of the lifts having an open peripheral face, and wide open top and bottom faces, and with each lift including declutchable means for locking its cartridge radially in position during centrifuging;

a plurality of reading gauges fixed to said hub level with respective ones of the peripheral faces of said lifts;

each cartridge is generally rectangular in shape and comprises:

a flexible sachet of plastic material having three compartments each intended to contain a reagent or a diluant with at least one of the compartments, referred to as an "analysis" compartment, being connected firstly to a free end of the sachet via a channel which is closed by a fragile capsule, and secondly to the other two reagent storage compartments via respective ducts each including a fragile closure;

a rectangular bottom preformed in plastic material to receive said sachet and also provided with a cuvette for storing serum, said channel of said sachet terminating in said cuvette said bottom including an opening therein;

a lid for closing said bottom and having an opening aligned with the opening in said bottom and leaving a major portion of said analysis compartment visible;

said processing device including at least one peripheral read module situated on the path of said gauges, a module situated above the path of said analysis compartments and reagent storage compartments, and provided with means for breaking said fragile capsules and said fragile duct closures.

Preferably, said processing device is associated with at least one pipette for automatically filling serum into the corresponding cuvettes of said cartridges. It may also include a module for automatically loading a cartridge into each lift, together with a module for automatic unloading.

In an improvement, said processing device includes a module provided with means for bearing against said flexible analysis compartment and homogenizing the liquids contained therein.

In a particular embodiment each reading gauge is constituted by a transparent gutter which is substantially U-shaped so as to block radial displacement of said flexible analysis compartment, said means for locking said cartridge in said lifts then being disengaged, and said U-shaped gutter having two horizontal side walls at a calibrated distance apart against which said analysis compartment bears during centrifuging.

By way of example, said sachet is constituted by a sheet of thermoformed Surlyn (trademark belonging to Du Pont de Nemours), folded in two and heat welded along lines defining said compartments and said channel.

In addition, said bottom and its lid may be interconnected along their sides by two guides which clamp them between pairs of lips.

BRIEF DESCRIPTION OF THE DRAWINGS

An embodiment of the invention is described by way of example with reference to the accompanying drawings, in which:

FIG. 1 is a perspective view of a three compartment sachet shown open and usable for constituting a cartridge in accordance with the invention;

FIG. 2 is a perspective view of the FIG. 1 sachet, shown closed;

FIG. 3 is an exploded perspective view of a cartridge in accordance with the invention;

FIG. 6 is a diagrammatic plan view of the FIG. 3 cartridge fully assembled;

FIG. 7 is a diagrammatic longitudinal side view of the FIG. 6 cartridge;

FIG. 8 is a diagrammatic end view of the FIG. 6 cartridge;

FIG. 9 is a view similar to FIG. 6, but is even more diagrammatic (cf.

FIGS. 16 to 21 are diagrams showing the various stages of a reaction taking place in a cartridge in accordance with the invention.

DETAILED DESCRIPTION

Figure 4:
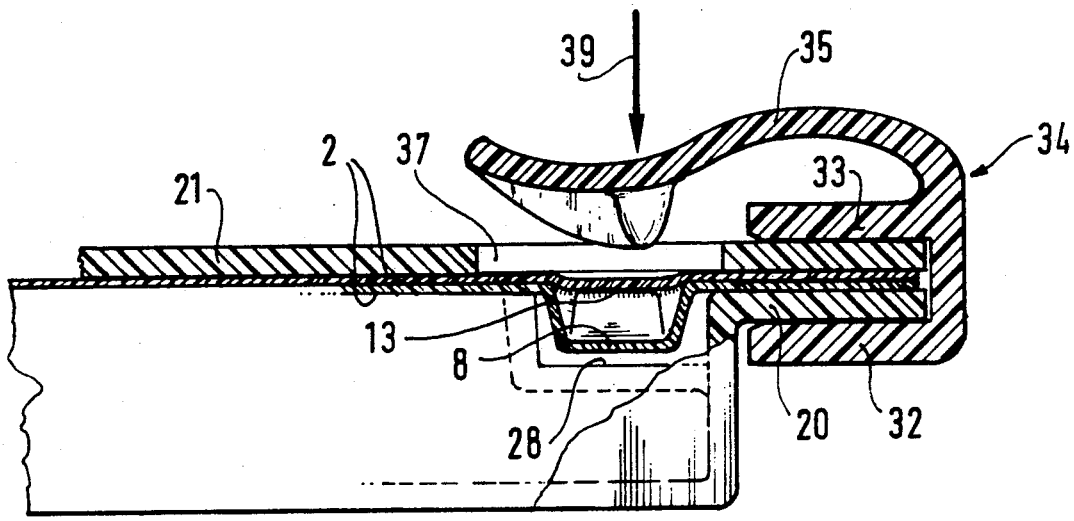
FIG. 4 is a fragmentary cross-section view showing a detail of a cartridge of the invention.

FIGS. 1 and 2 show a flexible, three-compartment sachet 10 respectively in an open position and in a closed position, said compartments being intended to receive reagents or diluants. Most analyses can be performed with less than three reagents. Depending on circumstances, at least one of the compartments in the sachet 10 may be empty. The sachet 10 is made from a rectangular sheet of very thin plastic material 2 which is folded in half about an axis 3.

The sheet 2 is thermoformed so as to define:

an analysis compartment 4 situated at one end of the sachet 10 and capable of communicating with the outside at the other end of the sachet via a channel 7 when a fragile capsule 15 which closes the channel 7 is broken; and two reagent-storing compartments 5 and 6 suitable for being put into communication with the analysis compartment 4 via respective ducts 8 and 9.

The two halves of the sheet 2 are hot welded together along a network of lines 11 shown dashed in FIG. 1. In zones the hot welding causes the ducts 9 and 10 to be obstructed, at least partially, and sets up fragile welds 12, 13 therein.

In the factory, before completely closing the compartments, they have reagents or diluants adapted to a given analysis inserted therein The sachet 10 prepared in this way is shown in FIG. 3 It is too flexible to be used directly in a processing device. That is why it is associated with a bottom 20 and with a lid 21 made of thin plastic material which is relatively stiff so as to constitute an analysis cartridge 1. The bottom 20 and its lid are considerably longer than the sachet 10. The bottom 20 is thermoformed so as to be a close fit over the various compartments 5 and 6, and over the channel 7. Thus, it includes cuvettes 25 and 26 corresponding to compartments 5 and 6, a channel 27 corresponding to channel 7, and ducts 28 and 29 corresponding to ducts 8 and 9.

The bottom 20 also has an opening 22 level with a portion of the analysis compartment 4 and a serum storage cuvette 23 communicating with the channel 27. The plane lid 21 has an opening 24 analogous to the opening 22 in the bottom 20, and an opening 30 providing access to the serum storage cuvette 23.

The bottom 20 and the lid 21 are fixed together, e.g. by means of two side guides 31 which clamp them between parallel lips 32 and 33.

In a zone 34 situated level with the ducts 9 and 10 having fragile welds 12 and 13, each of the guides is provided with means for breaking the adjacent weld, and these means are more clearly visible in FIG. 4. The top wall 35 of the guide 31 is partially disconnected in the zone 34 by two cuts 36 and may be pressed in the direction of arrow 39 against the fragile weld 13 through an opening 37 made in the lid 21, thereby breaking the weld and reopening the duct 8.

Figure 5:
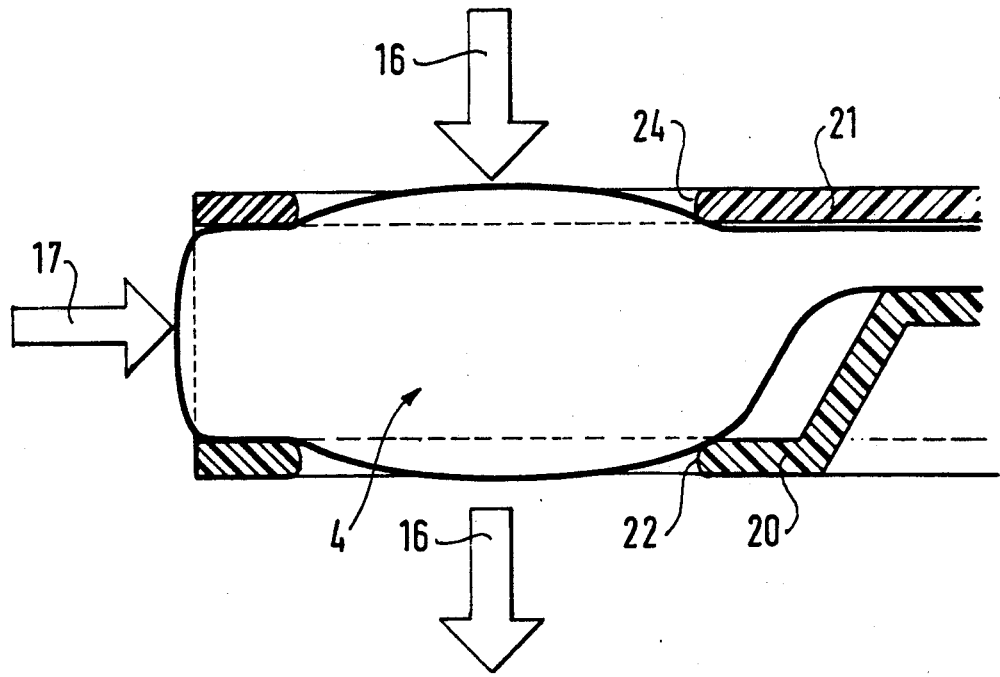
FIG. 5 is a fragmentary longitudinal section through the analysis compartment of a cartridge in accordance with the invention.

FIG. 5 is a highly diagrammatic longitudinal section on a larger scale through the analysis compartment 4 of the sachet 10 showing the transparent walls enabling the inside of the compartment to be observed by any appropriate reading device looking along the direction of arrows 16 or 17.

FIGS. 6 to 8 are diagrams showing three faces of a fully assembled FIG. 3 cartridge 1 ready for use.

FIG. 9 is a diagram of the cartridge suitable for explaining its operation, as is done below with reference to FIGS. 16 to 21.

The above-defined cartridge 1 provided with its own identification means is processed in a device 40 shown in FIGS. 10 to 15 and constituting a mini-laboratory. It is generally in the form of a rectangular box 50 having a square base of size 300 mm × 300 mm and a height of about 200 mm.

This processing device may optionally be placed inside a thermostatically controlled enclosure.

The main subassemblies of the device 40 are as follows (cf. FIGS. 10 and 11):

A hub 41 suitable for being rotated on a shaft 46 by a motor 43 having a transmission system shown diagrammatically at 42 and constituting a cog belt and two toothed wheels. The motor is a D.C. motor associated with an angle encoder 45 for controlling cycles of rotation.

The hub 41 is fixed to twelve cartridge-carrying lifts such as 51, which are uniformly distributed radially around the hub. Each cartridge-carrying lift 51 is associated with a control system 53 for moving the cartridge-carrying lift 51 from a raised position 51' shown in dashed lines to a lowered position shown in solid lines. The control system 53 may be constituted by a controllable electromagnet 54 associated with a lever 55. The positions 54' and 55' of the electromagnets and the lever corresponding to the position 51' of the cartridge-carrying lift 51 are likewise shown in dashed lines. Return springs 56 are provided between the lifts 51 and the top face 57 of the hub 41.

Figure 10:
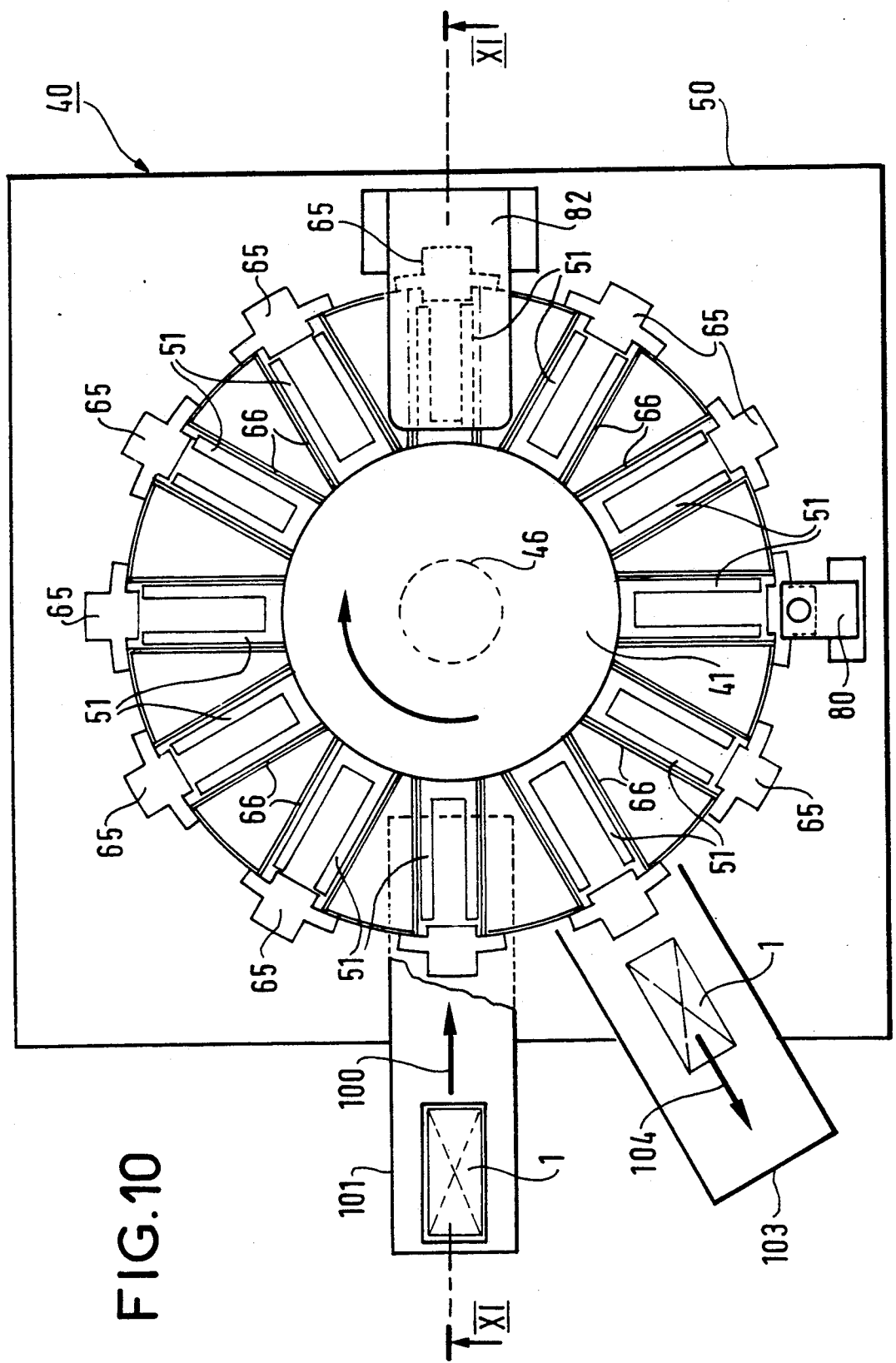
FIG. 10 is a diagrammatic plan view of a processing device for processing the above cartridges.

When the lift is in position 51', a cartridge 1 may be manually inserted thereon along arrow 100 as shown in FIG. 10. However this insertion is preferably performed automatically by an automatic loading module 101 (with drive shown diagrammatically at 102). Similarly, there is an automatic unloading module 103 for unloading in a direction shown diagrammatically by arrow 104, as shown in FIG. 10.

Figure 12:
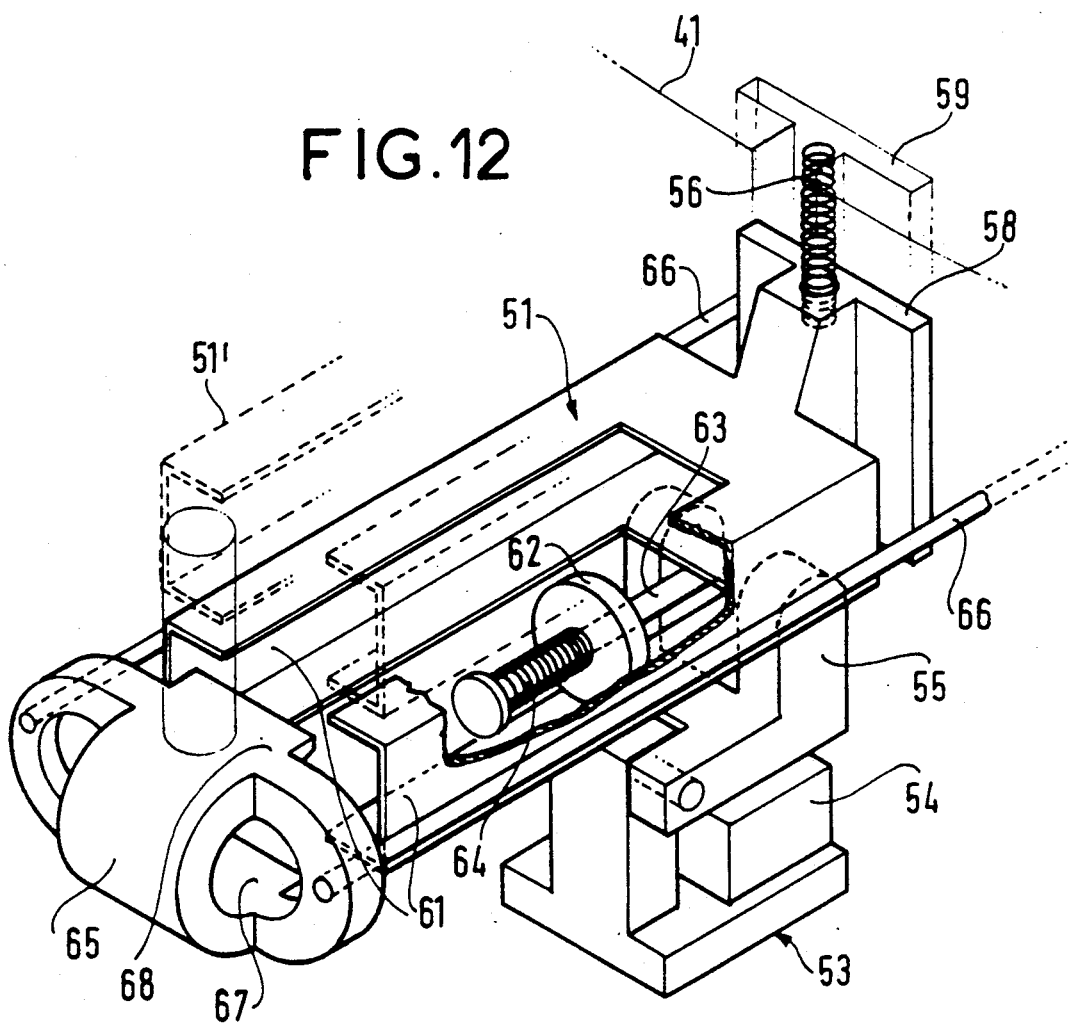
FIG. 12 is a diagrammatic perspective view of a cartridge-carrying lift for the device of FIGS. 10 and 11.

FIG. 12 shows a lift 51 more clearly comprising a T-shaped portion 58 guided in a corresponding groove 59 in the hub 41. At its opposite end, the lift 51 has an open inlet face, and its two side portions are constituted by channel section rails 61 leaving its top face wide open. The same applies to its bottom face through there passes a cartridge indexing disk 62 suitable for sliding along a rod 63 fixed to the hub 41 and co-operating with a return spring 64 which is clearly visible in FIG. 13. This figure also shows a notch 74 provided in the cartridge 1 suitable for receiving the disk 62. The system is suitable for driving the cartridge 1 towards the outlet face of the lift 51 in the direction of arrow 69. In contrast, the system shown in FIG. 14 and co-operating with an orifice 70 in the cartridge 1 is intended to retain the cartridge towards the center of the hub 41 when the system is in its position shown in solid lines. The latch system comprises a moving arm 72 associated with a return spring 75 and actuated by a control electromagnet 71. The arm 72 may move into position 72', whereupon its end 73 which was inserted in the orifice 70 then takes up position 73' outside the orifice releasing the cartridge. The cartridge 1 is then displaced by the system of FIG. 13 which guides it radially towards the periphery of the device 40.

On the peripheral portion of the device 40 and level with each inlet face to a lift 51, there is an optical reader gauge 65 fixed to the hub 41, e.g. by means of rods 66

Figure 11:
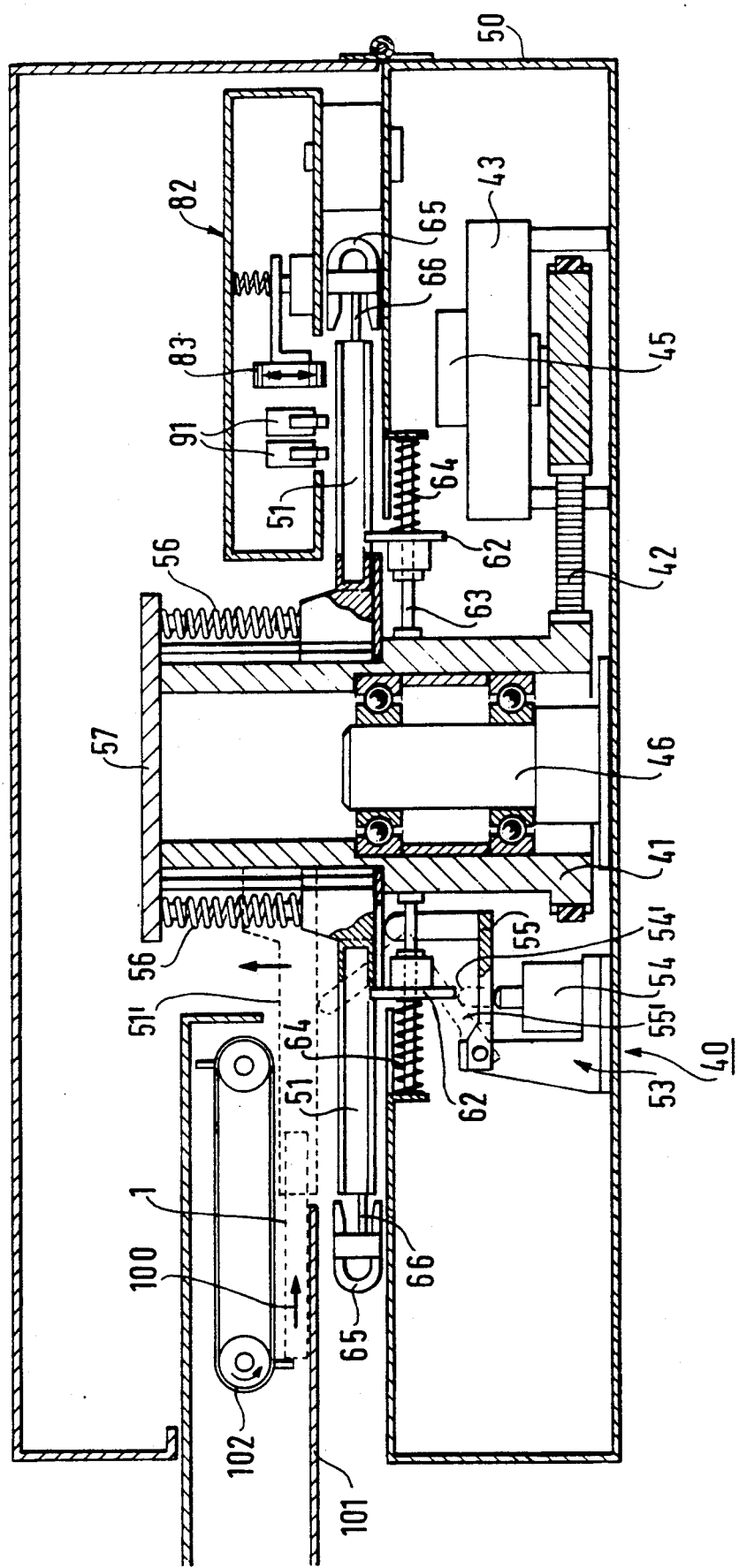
FIG. 11 is a diagrammatic section on line XI—XI of FIG. 10.

(see FIGS. 10 to 12). Each gauge 65 is a substantially U-shaped gutter or part with an accurately calibrated gap between its side walls 67 and 68 (cf. FIG. 12). The part may be made of perfectly transparent injected polycarbonate.

FIG. 10 shows a module 80 for reading reactions by colorimetry or by luminescence or by any other appropriate method, by optically looking through the gauges 65.

Figure 15:
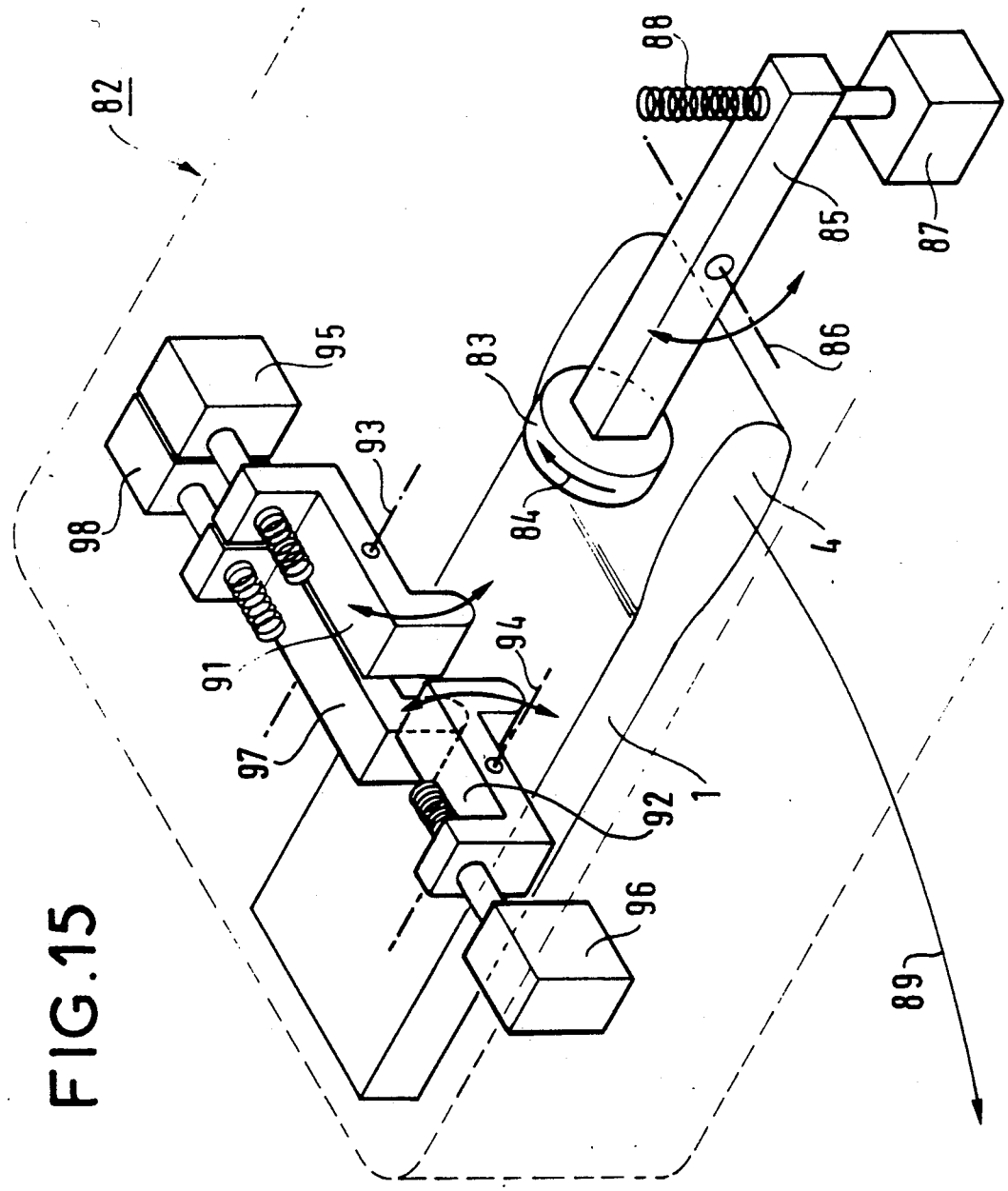
FIG. 15 is a diagrammatic perspective view of a module belonging to the above processing device.
Figure 16:
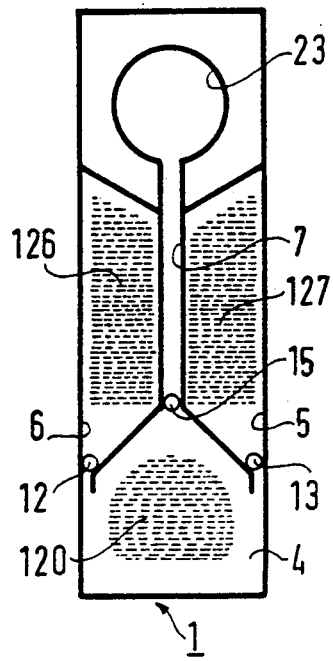
FIGS. 16 to 21)
Figure 17:
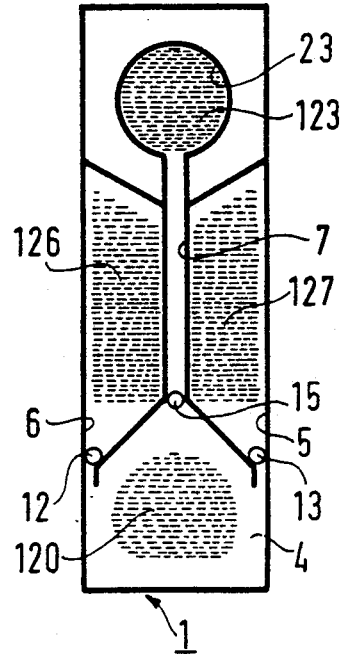
Figure 18:
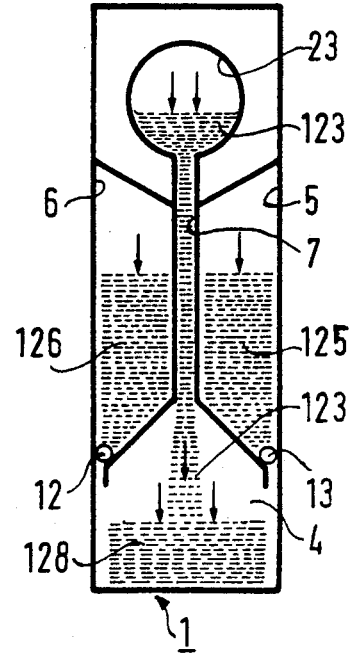
Figure 19:
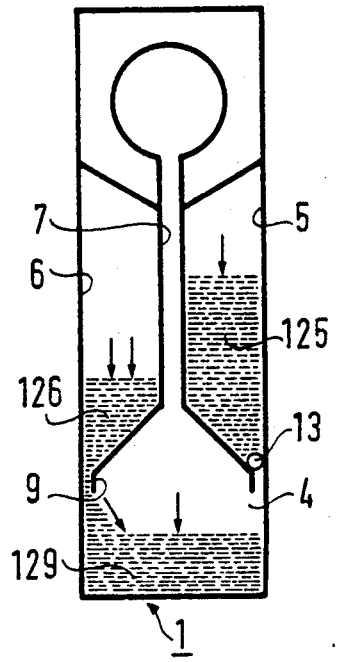
Figure 20:
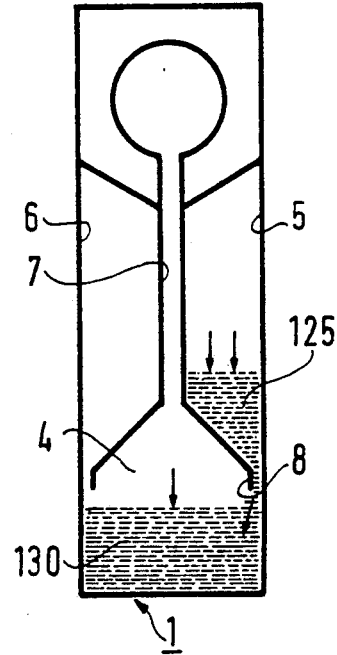
Figure 21:
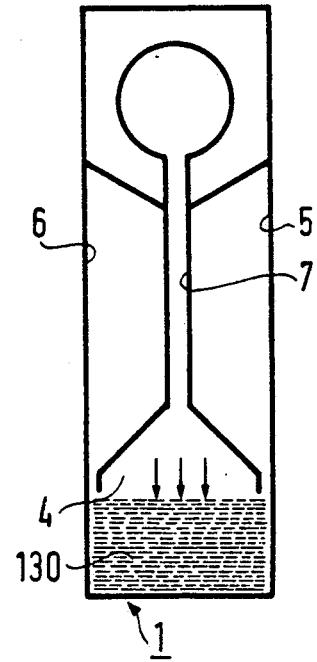

This figure also shows a module 82 which is shown in greater detail in FIG. 15. This module comprises firstly a roller wheel 83 rotatable in the direction of arrow 84 and fixed to an arm 85 which is rockable about an axis 86, thereby enabling the roller wheel 83 to be retracted. The arm is controlled by an electromagnet 87 and by a return spring 88 fixed to the module 82. The roller wheel 83 is level with the trajectory 89 of the reaction compartment 4. Its function, during a centrifuging operation, is to crush a portion of the compartment 4 in order to move the liquid contained therein, and then to let it return to its original shape, etc. . . ., thereby homogenizing the liquid.

The module 82 also includes hammers 91 and 92 rockable about respective axes 93 and 94 by electromagnets 95 and 96. These hammers are situated over the fragile welds 12 and 13, and more precisely over the zones 34 in the guides 31 as described above. The hammers are used to bear against these zones and to open the ducts 8 and 9 of the sachet 10. A hammer 97 analogous to the above hammers is also provided over the fragile capsule 15. When operated by an electromagnet 98, it breaks the capsule.

The various stages of using a cartridge 1 in the processing device 40 are described below with reference to FIGS. 16 to 21.

When the cartridge 1 is inserted by the automatic loading module 101 into a cartridge-carrying lift in raised dotted line position 51' (FIG. 11), it is in the state shown in FIGS. 6 to 8, including its sachet 10 of reagents suitable for the analysis to be performed. Three reagents 126, 127, and 120 are referenced, however at least one of them may be constituted by a diluant, and at least one of the compartments may be empty, depending on the intended type of analysis.

Figure 13:
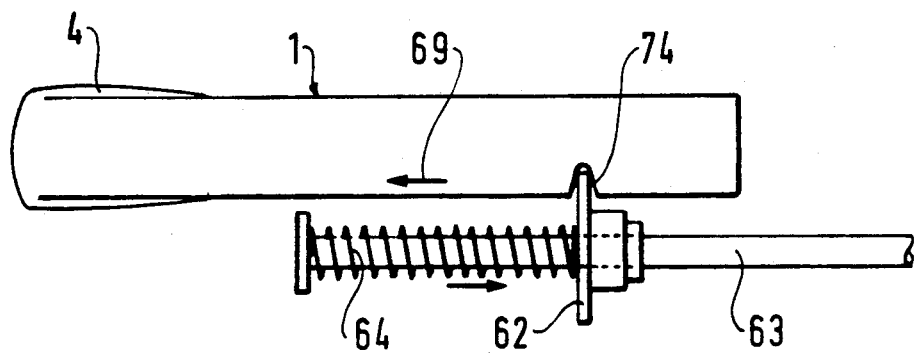
FIG. 13 is a diagrammatic side view of a first cartridge return system belonging to the cartridge-carrier lift of FIG. 12.
Figure 14:
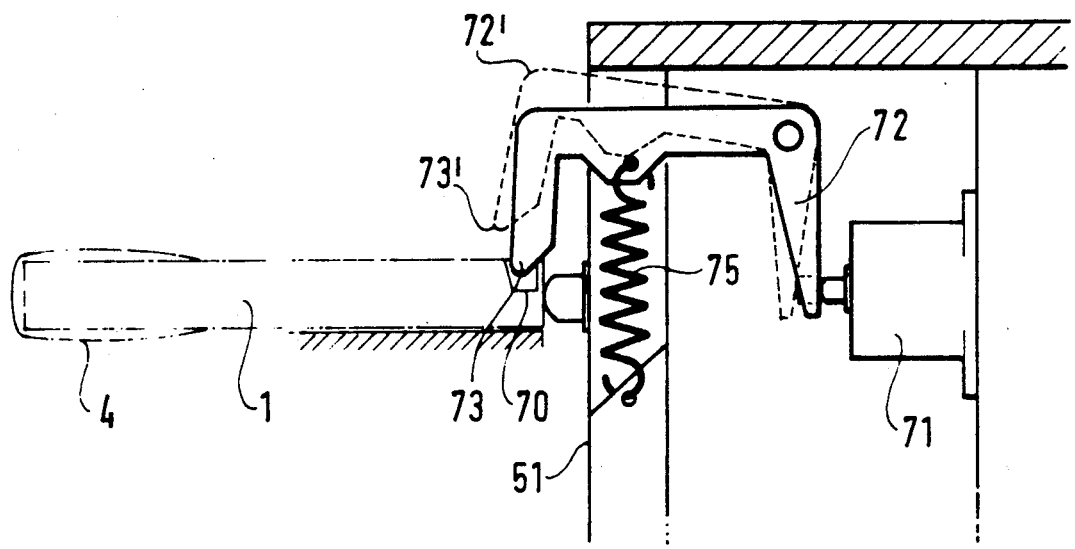
FIG. 14 is a diagrammatic side view of a second cartridge return system belonging to the cartridge-carrier lift of FIG. 12.

When the cartridge 1 is loaded, its orifice 70, FIG. 3, and its notch 74 (FIG. 13) are engaged by the latching and cartridge return systems shown in FIGS. 13 and 14, respectively.

When the cartridge-carrying lift has returned to its position 51, the motor 43 rotates the hub 41 through onetwelfth of a turn so that a following cartridge can be loaded (FIGS. 10 and 11). While the second cartridge is being loaded, it is advantageous to insert serum 123 into the serum storage cuvette 23 of the first cartridge (cf. FIG. 17). This may be done automatically, e.g. by using the pipette described in the Applicant's French patent number 87 15688.

Once a set of cartridges has been loaded, the fragile capsule 15 closing the channel 7 in each sachet 10 is broken by passing each cartridge 1 through the module 82, where the capsule is broken by the hammer 97, FIG. 15. A centrifuging operation is then performed to cause the serum 123 to flow along the channel 7 into the analysis compartment 4 (cf. FIG. 18). This compartment then contains a mixture 128.

The cartridge 1 returns to the module 82 in order to break fragile weld 12 and open duct 9, i.e. hammer 92 acts on corresponding zone 34 of the cartridge (cf. FIGS. 15 and 4). A new centrifuging operation is performed in order to cause the reagent 126 to flow from the compartment 6 into the analysis compartment 4 (cf. FIG. 19). The analysis compartment 4 then contains a mixture 129.

An operation identical to that performed on weld 12 is repeated to break fragile weld 13 by passing the cartridge 1 through the module 82 and actuating the hammer 91. The duct 8 is then opened. A further centrifuging operation is performed in order to cause reagent 125 to move into the analysis compartment 4 (see FIGS. 20 and 21). This compartment then contains a mixture 130. The mixture is then homogenized by passing the cartridge 1 beneath the module 82 and switching on its rolling wheel 83. The cartridge is then ready to have the mixture 130 optically read.

The electromagnet of FIG. 14 acts on the arm 72 which moves to position 72' to release the cartridge 1 which is then urged towards the periphery of the device by the spring 64 shown in FIG. 13. Under the effect of centrifuging, analysis compartment 4 (cf. FIG. 5) partially filled with liquid 130 then presses against the plane walls 67 and 68 at a calibrated distance apart in the gauge 65 associated therewith (cf. FIG. 12). A colorimetry, or a luminescence, or other appropriate measurement is then optically performed when the cartridge 1 enters the measurement module 80, FIG. 10. This will provide a value for the substance to be measured in the serum.

The operations performed by the device 40 are controlled by a programmed computer or microprocessor.

By way of example, a cartridge may have the following dimensions:

length about 50 mm;
width about 15 mm; and
height about 5 mm to 6 mm.

The quantities of serum and reagents used are of the order of about 10 microliters to a few hundred microliters. These analyses may be performed with very small quantities of serum, of the order of a few hundred microliters, given the measurement accuracy possible with current pipettes. The flexible sachet is preferably made of SURLYN, a thermoplastic synthetic resin (registered trademark in the name of E.I. Du Pont de Nemours and Company), having a thickness of 40 micrometers. The bottom and the lid are made of polystryene, for example.

In order to simplify the drawing, only twelve cartridge-carrying lifts are shown, however the dimensions specified enable eighteen to be installed, and this number is merely another example.

The device of the invention enables an operator to store several tens of cartridges in a magazine corresponding to each of the analyses which normally need to be performed. By using the processing device 40, it is possible for the operator to perform all of the operations required for chemical analysis of serum automatically.

A few examples of such analyses are given below.

EXAMPLE I

Analysis using a single reagent: measurement of urinary creatinine.

10 to 25 microliters of sample are used. The reagent is of the CPK (creatine phosphokinase), or of the LDH (lactodeshydrogenase) type. After allowing the reagent time to operate, the reading module gives the result at a given wavelength.

EXAMPLE II

Two reagent analysis: measuring uric acid.
20 microliters of serum are used.
The first reagent (chromogenic buffer) has the following composition:
phosphate buffer at pH 7.0: 150 mmol/l:
3,5 dichloro-2-hydroxy-benzene sulfonic acid: 2 mmol/l; and
surface active agent: 2 mmol/l.
500 microliters are added. The reaction lasts for three minutes.
The second reagent (enzymes) has the following composition
uricase: $\geq 100$ U/l
peroxydase: $\geq 200$ u/l
amino-4-antipyrine: 0.25 mmol/l.
5 microliters are added. The reaction lasts for three minutes. The results are then read using a photometer at 340 nanometers.

EXAMPLE III

Analysis using three LHD (Lacto-deshydrogenase) reagents.
5 microliters of serum are used.
The first reagent (buffer) has the following composition:
tris buffer with a pH of 7.2: 80 mmol/l
NaCl: 200 mmol/l.
250 microliters are inserted.
250 microliters of the second reagent (NaOH coenzymes at 0.2 mmol/l) is inserted. After one minute, 50 microliters of the third reagent is inserted (pyruvate at 1.6 mmol/l). The reaction is observed during its first two minutes.

Naturally, the invention is not limited to the embodiments described and shown. Without going beyond the scope of the invention, any means may be replaced by equivalent means.

I claim:

1. An apparatus for processing a plurality of cartridges by performing biological analyses by chemical reaction on a serum, said apparatus comprising:
   a hub mounted for rotation about the axis of the hub, connected to a motor and having an angle encoder controlling rotation cycles of said hub and imparting both centrifuging motion to the hub and also step-by-step motion thereto;
   a plurality of circumferentially spaced cartridge-carrying lifts fixed radially to the hub and supporting said cartridges, respectively, means for causing each lift to pass from a cartridge-loading position to a working position, said cartridge-loading position being higher than said working position, each of the lifts having an open peripheral face, and aligned open top and bottom faces, and each lift including declutchable means for locking a cartridge radially in position during centrifuging;
   a plurality of optical reading gauges at said circumferentially spaced positions of said lifts, fixed to said hub and level with the peripheral faces of said lifts, respectively, and rotatable therewith;
   each cartridge being of generally rectangular shape and comprising:
   a flexible sachet of flexible plastic material having three compartments each intended to contain a reagent or a dilutant, with at least one of the compartments being a flexible analysis compartment optically aligned with said optical reading gauge, being connected firstly to a free end of the sachet via a channel closed by a fragile capsule, and secondly to the other two reagent storage compartments via respective ducts, each including a fragile weld;
   a rectangular bottom preformed in plastic material receiving said sachet, having an opening aligned with said sachet analysis compartment and being also provided with a cuvette for storing serum, said channel of said sachet terminating in said cuvette;
   a lid closing said bottom, said lid having an opening aligned with said opening within said bottom leaving a major portion of said analysis compartment visible for facilitating optical measurement of reagent condition in said analysis compartment;
   said apparatus further comprising at least one peripheral optical read situated on the path of rotation of said optical reading gauges for selective alignment with said optical reading gauges and performing an optical measurement of the condition of reagent mixture within an analysis compartment upon effecting such alignment means and a cartridge fragile capsule and weld breaking module situated above the path of movement of said analysis compartment and reagent storage compartments, provided with means for selectively breaking said fragile capsule and said fragile duct welds.

2. Apparatus according to claim 1, wherein said processing device is operatively associated with at least one pipette including means for automatically filling serum into the corresponding cuvettes of said cartridges.

3. Apparatus according to claim 1, wherein said processing device further includes a loading module positioned along the path of movement of said lifts having means for automatically loading a cartridge into each lift upon alignment therewith.

4. Apparatus according to claim 1, further including an unloading module positioned along the path of movement of said lifts for automatically unloading the cartridges.

5. Apparatus according to claim 1, further including a liquid homogenizing module positioned along the path of movement of said lifts and provided with means for compressibly bearing against said flexible sachet analysis compartment for homogenizing the liquids contained therein.

6. Apparatus according to claim 1, wherein each reading gauge is constituted by a transparent gutter which is substantially U-shaped and positioned to block radial displacement of said sachet flexible analysis compartment, said gutter having two horizontal side walls at a calibrated distance apart against which said analysis compartment bears during centrifuging.

7. Apparatus according to claim 1, wherein said sachet is constituted by a sheet of thermoformed plastic folded in two and heat welded along lines defining said compartments and said channel.

8. Apparatus according to claim 1, wherein said bottom and said lid are interconnected along their sides by pairs of lips of two guides which clamp said bottom and lid between said pairs of lips.

* * * * *